United States Patent
Erbe et al.

(12) 
(10) Patent No.: US 6,375,659 B1
(45) Date of Patent: Apr. 23, 2002

(54) METHOD FOR DELIVERY OF BIOCOMPATIBLE MATERIAL

(75) Inventors: Erik M. Erbe, Berwyn; Antony Kobilish, Malvern; Maarten Persenaire, Phoenixville, all of PA (US)

(73) Assignee: Vita Licensing, Inc., Wilmington, DE (US)

( * ) Notice: Subject to any disclaimer, the term of this patent is extended or adjusted under 35 U.S.C. 154(b) by 0 days.

(21) Appl. No.: 09/788,930

(22) Filed: Feb. 20, 2001

(51) Int. Cl.$^7$ .................................................. A61F 5/04
(52) U.S. Cl. ........................ 606/94; 606/93; 623/23.62; 623/23.73
(58) Field of Search ............................. 606/94, 92, 93, 606/95, 99, 102; 623/23.48, 23.46, 23.21, 23.22, 23.62, 23.73, 22.12

(56) References Cited

U.S. PATENT DOCUMENTS

| | | | |
|---|---|---|---|
| 6,019,765 A | * | 2/2000 | Thornhill et al. |
| 6,033,411 A | | 3/2000 | Preissman ..................... 606/99 |
| 6,048,343 A | * | 4/2000 | Mathis et al. .................. 606/92 |
| 6,019,776 A | | 12/2000 | Preissman et al. ........... 606/185 |
| 6,231,615 B1 | * | 5/2001 | Preissman ................ 623/23.73 |
| 6,248,110 B1 | * | 6/2001 | Reiley et al. ............. 606/23.62 |
| 6,273,916 B1 | * | 8/2001 | Murphy .................... 623/23.62 |

OTHER PUBLICATIONS

Chiras, J., et al., "Percutaneous Vertebroplasty, " *J. Neuroradiol.*, 1997, 24, 45–59 (English translation).

Deramond, H., et al., "Percutaneous Vertebroplasty," *Seminars in Musculoskeletal Radiology*, 1997, 1(2), 285–295.

Gangi, A., et al., "Percutaneous vertebroplasty guided by a combination of CT and fluoroscopy," *AJNR*, Jan. 1994, 83–86.

Heini, P.F., et al., "Percutaneous transpedicular vertebroplasty with PMMA: operative technique and early results: A prospective study for the treatment of osteoparotic compression fractures,"*Eur. Spine J.*, 2000, 9, 445–450.

Jensen, M.E., et al., "Percutaneous polymethylmethacrylate vertebroplasty in the treatment of osteoporotic vertebral body compression fractures: technical aspects," *AJNR*, Nov. 1997, 18, 1897–1904.

* cited by examiner

*Primary Examiner*—Pedro Philogene
(74) *Attorney, Agent, or Firm*—Woodcock Washburn LLP

(57) ABSTRACT

Novel methods for the delivery of biocompatible material to intraosseous spaces are provided comprising accessing a space, placing a first aliquot of restorative material into the space, and after a period of time sufficient for first aliquot to set, placing a second aliquot into the space.

15 Claims, 4 Drawing Sheets

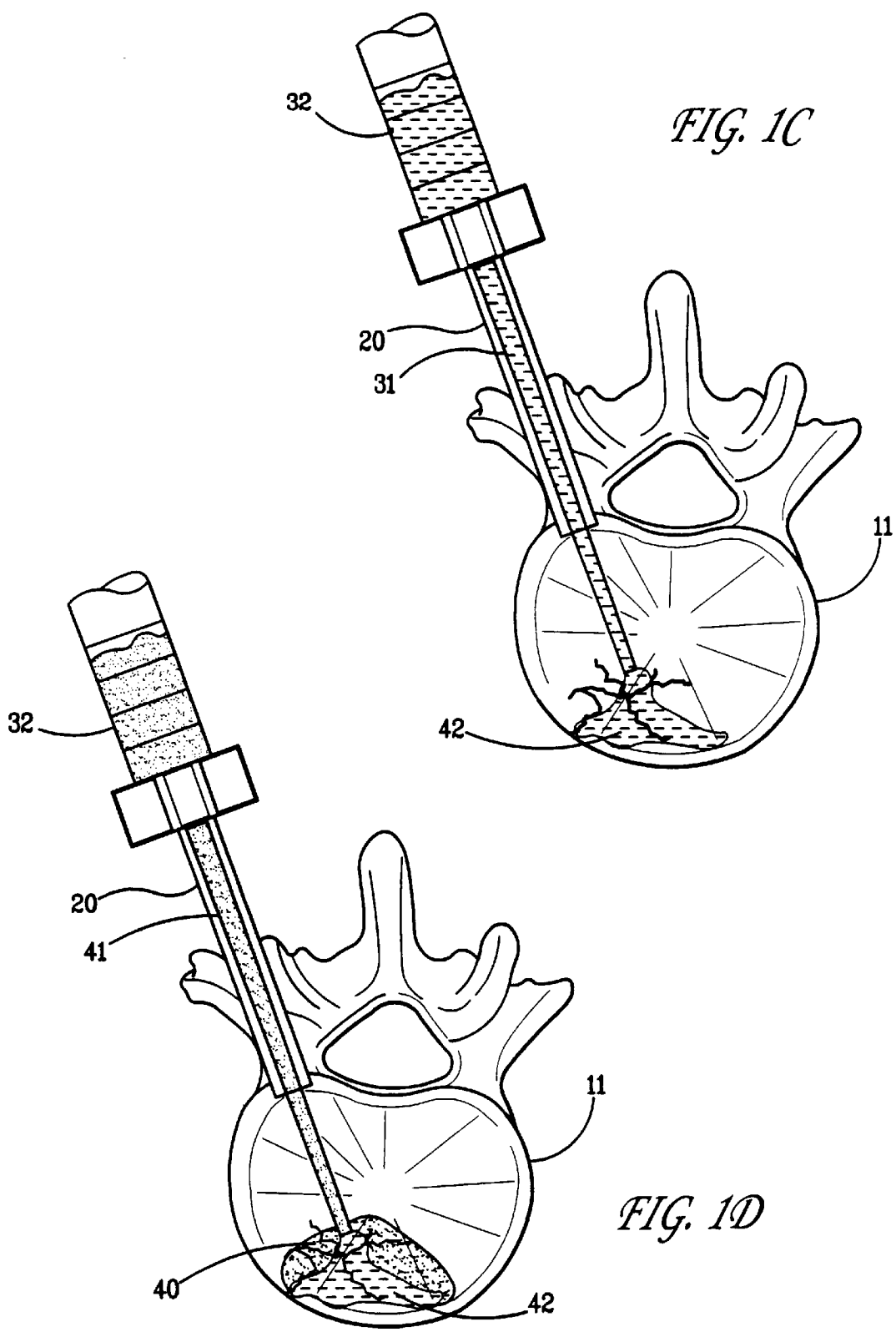

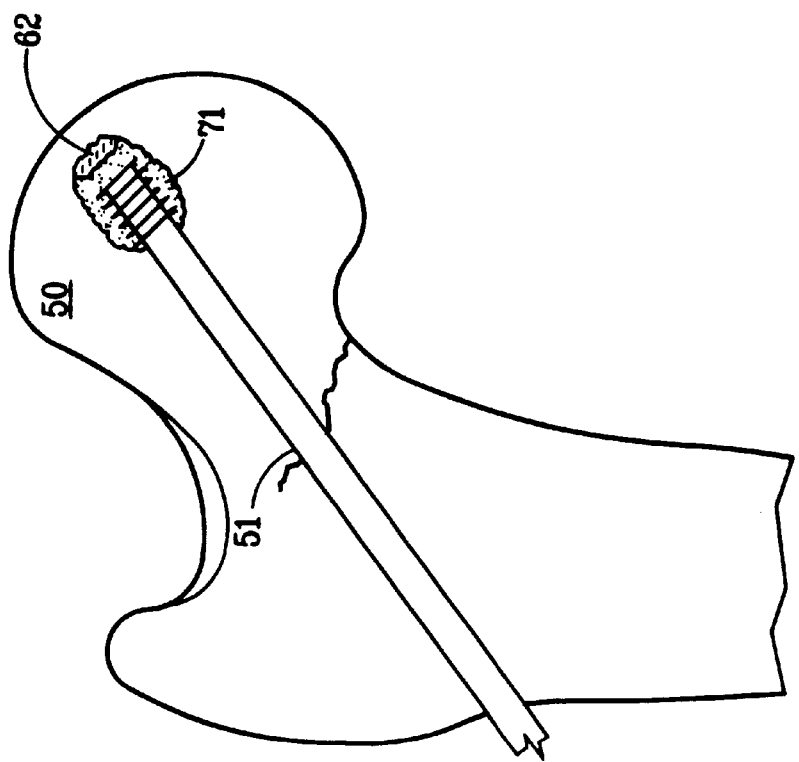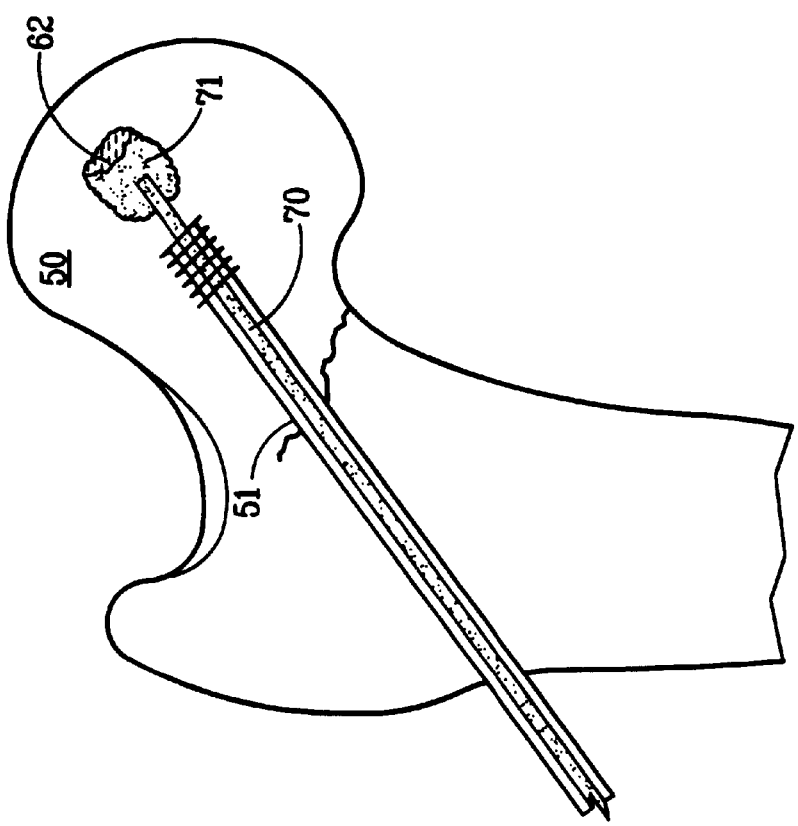

METHOD FOR DELIVERY OF BIOCOMPATIBLE MATERIAL

FIELD OF THE INVENTION

This invention relates to methods for the restoration of intraosseous spaces as well as methods for the reparation of bony defects, fractures and surgically created defects. The invention relates to methods for restoring intraosseous spaces in percutaneous surgical procedures, such as percutaneous vertebroplasty, and in the repair of fractures in procedures such as those requiring screw augmentation, including cannulated screw augmentation.

BACKGROUND OF THE INVENTION

Percutaneous surgical procedures have come to the forefront of the orthopaedic and neurological surgery fields, in an effort to limit exposure of tissues, reduce operating time, speed up recovery time and minimize patient scarring. Percutaneous vertebroplasty is a procedure by which, currently, acrylic cement, typically polymethylmethacrylate ("PMMA"), is injected into the vertebral body by a percutaneous route in order to prevent vertebral body collapse and pain in patients with unhealthy vertebral bodies. Percutaneous injection has been indicated as a means of pain relief and restoration in patients with vertebral hemangiomas, painful vertebral body tumors, as well as painful osteoporosis with loss of height and/or compression fractures of the vertebral body. See, e.g., Gangi, A., et al. *Percutaneous Vertebroplasty Guided by a Combination of CT and Fluoroscopy*, AJNR 15:83–86, January 1994 ("Gangi"). All references cited in this specification are incorporated herein by reference. Percutaneous injection is also minimally invasive compared to the alternative of exposing the entire soft and hard tissue at the surgical site.

U.S. Pat. Nos. 6,033,411 and 6,019,776 to Preissman, et al. disclose methods for controlled approach to the interior of a vertebral body by inserting a threaded or sharp-pointed stylet and cannula percutaneously through the soft tissue of an organism until abutting the soft tissue; further inserting the stylet into a predetermined location within the hard tissue; ratcheting a pawl mechanism or rotating a camming mechanism to advance the cannula along the stylet to the predetermined location; withdrawing the stylet from the cannula and attaching a source of implantable material for injection of the material into the organism through the cannula. However, these patents do not teach methods of delivering restorative material by percutaneous vertebroplasty in which several doses of material are injected.

Heini, P. F. et al., *Percutaneous Transpedicular Vertebroplasty with PMMA: Operative Technique and Early Results: A Prospective Study for the Treatment of Osteoporotic Compression Fractures*, Eur. Spine J. (2000) 9:445–450 ("Heini"), discusses the use of PMMA for percutaneous vertebroplasty and disclose the surgical practice of using four injections (i.e., injecting four vertebrae unipedicularly or two vertebrae bipedicularly) in one session under local anesthesia. The procedure disclosed, states that within "two minutes into the cement curing, filling is commenced and then the material remains injectable for the following 2 or 3 minutes." Heini further cautions that the flow of cement must be monitored carefully for leakage posteriorly into the spinal canal and anteriorly through the nutritional vessels. Heini also teaches that only low-viscosity PMMA is suitable for injection and that the radio-opaqueness of injectable calcium phosphate makes its use technically difficult to achieve.

Deramond, H., et al., *Percutaneous Vertebroplasty*, Seminars In Musculoskeletal Radiology, Vol.1, No.2, 1997: 285–295 ("Deramond"), Chiras, J., et al., *Percutaneous Vertebroplasty*, J Neuroradiol, 1997, 24, 45–59 ("Chiras"), Jensen, M. E., et al., *Percutaneous Polymethylmethacrylate Vertebroplasty in the Treatment of Osteoporotic Vertebral Body Compression Fractures: Technical Aspects*, AJNR 18:1897–1904, November 1997 ("Jensen"), and Gangi describe the percutaneous injection of PMMA into the vertebral body with the aid of CT and/or fluoroscopic guidance. Prior to injecting the material, each method describes the step of preparing the injectable acrylic cement material. As described by Gangi, in order to prevent distal venous migration, the acrylic cement has to be injected during its pasty polymerization phase (page 84). Further, since the surgeon is required to wait until the material reaches the pasty polymerization phase, "the intervention [has] to be performed quickly, because the glue [begins] to thicken after 3 minutes, and any further injections [become] impossible." During material injection, the procedure is immediately stopped if an epidural or paravertebral opacification (under strict lateral fluoroscopy) is observed to prevent spinal cord compression. Deramond suggests that a leakage can be avoided by making injections under lateral fluoroscopic control or inserting the needle into the lateral part of the vertebral body. Jensen also teaches that the material should set only if a leak should occur.

In the prior art, if a leak is detected, the operator either stops the procedure altogether, continues with the injection of more material using a different "batch" of material, or allows the material that already has been injected to thicken. Clinically, using a different "batch" of material requires opening another "batch" of material. This is costly and not desirable or practical in the case of standard restorative materials such as PMMA. If the surgeon does not allow the material to set, but rather merely allows it to thicken, which is more often the case, then he is forced to work quickly and often cannot deliver the desired amount prior to all the material's setting. Forceful injection is required to add additional material prior to the material's setting. Another problem with procedures of the prior art is that a catheter is rarely used. If the material hardens, it will also harden in the cannula where it would have to be removed for the injection of additional doses. Surgeons are very skeptical about doing this because of the extreme difficulty in reinserting another cannula in the exact place as the one removed.

It is the principle object of this invention to provide methods for the restoration of intraosseous spaces. It is a further object of the invention to provide methods of controlled injection of restorative material into a vertebral body to prevent leakage of that material into the venous space. It is yet another object of the invention to provide minimally invasive techniques for the reparation and restoration of bony structures and to provide minimally invasive techniques for the augmentation of procedures requiring screw fixation.

Additional objects, advantages and novel features of this invention will become apparent to those skilled in the art upon examination of the following descriptions, figures and claims thereof, which are not intended to be limiting.

SUMMARY OF THE INVENTION

This invention relates to methods for restoring an intraosseous space comprising the steps of accessing a space, placing in the space a first aliquot of restorative composition, and, after a period of time sufficient for the first aliquot to set, placing in the space a second aliquot of restorative composition. The first aliquot placed into the space to initiate the restorative process can be preselected. There are preferably additional aliquots of restorative composition placed into said space. These additional placements of composition can follow preselected time intervals and be of a preselected amount. The placements within these methods are preferably made using a syringe and catheter via a needle or cannula that is inserted in the intraosseous space. The location of the instrumentation as well as the material in the intraosseous space is easily monitored via fluoroscopy or endoscopy. In one embodiment, the catheter has a distal end and at least one placement orifice disposed proximate to said distal end, said placement orifice being adapted for dispensing the restorative composition radially from the catheter. The space is accessed via drill, knife, or needle.

BRIEF DESCRIPTION OF THE DRAWINGS

FIGS. 1a–1d are sectional views showing steps in one embodiment of the present invention method in which a needle/cannula is inserted into a damaged vertebral body to first deliver a dam of material and then deliver a subsequent dose to complete the reparation.

FIGS. 2a–2f depict the steps of an alternative embodiment of the present invention in which material is injected percutaneously through a cannulated screw.

DETAILED DESCRIPTION OF THE INVENTION

Figure 1A:
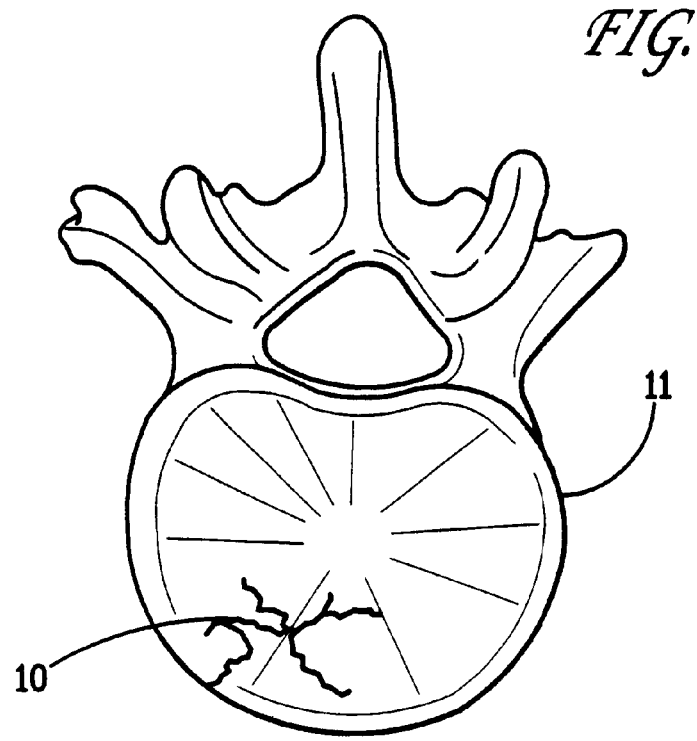
Figure 1B:
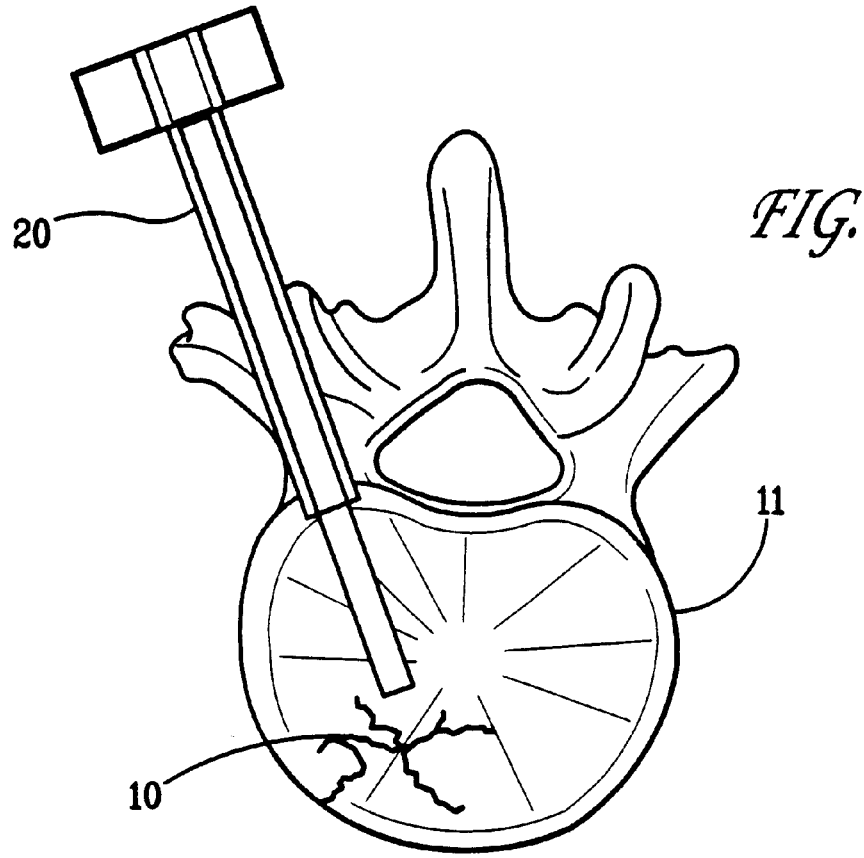

This invention provides methods for the delivery of restorative biocompatible material into intraosseous spaces. The methods generally comprise accessing a chosen intraosseous space, such as a damaged area 10 of vertebral body 11 depicted, for example, in FIG. 1a, placing an initial aliquot of the composition into said space; and, after a period of time adequate for the first aliquot to set, placing in the space, a second aliquot of a more sufficient dosage to restore the intraosseous space. The space can be accessed via a needle or cannula 20 (see, for example, FIG. 1b) and stylet, knife, or other sharp instrument depending on the procedure and space. In many embodiments, the space is accessed using a micro-reamer or drill. In other specific embodiments, the space is accessed using a cannulated screw (see FIGS. 2a through 2f).

According to a specific embodiment of the present invention, in cases where the existing bone is soft or porous (e.g., osteoporotic bone), the intraosseous space is accessed either by drilling out existing peripheral bone or by manually using a sharp instrument (such as a needle or cannula having a blunted, diamond or beveled tip). The needle serves as a guide for a stylet or mandarin that fits into the hollow cavity of the needle. More specifically, the stylet is provided with a pedestal on one end, which is impacted to advance the needle into position for delivery. In some embodiments, the stylet has a locking mechanism integral to the pedestal for locking securely to one end of the needle. In others, the tip of the stylet is beveled to provide steering capabilities or is diamond shaped. Insertion of the instruments is carefully monitored via standard imaging techniques to insure proper positioning and to prevent damage to surrounding structures.

In some preferred embodiments, once the desired position is reached, the stylet is removed with the needle in place and a micro-reamer is inserted into the hollow cavity. Generally, the micro-reamer is provided with a knob for dextrous manipulation and impacting on one end and a sharp cutting tip on the other and serves to make the channel for the catheter 31 and, as such, the eventual delivery of material. Once the channel is created, the catheter 31 is inserted (see, for example, FIG. 1c). With the use of a syringe 32, material is delivered via the catheter 31, such that a first aliquot of generally between 0.5–1.5 cc (and all combinations and subcombinations of ranges and specific volumes therein) is injected to establish a dam 42 and then subsequent aliquots are delivered for reparation.

Typically, once the space is accessed, an operator goes in with a catheter 31 (which sits within the bore of the cannula and extends out the tip of the cannula into the space) and augments the intraosseous space with the first aliquot of a restorative composition. The augmentation generally begins with an initial dam 42 being created by a small dosage of composition, the amount of which depends upon the osseous space being augmented, but typically is on the order of 0.5–1.5 cc (and all combinations and subcombinations of ranges and specific volumes therein). This dam is created to prevent additional dosages of those materials with a very mobile rheology, or high viscosity, from "leaking out." In a more typical embodiment, the location of the placement of this initial aliquot is pre-selected so as to initiate the restorative process and is monitored via standard radiography/fluoroscopy techniques for leakage.

The dam aspect in certain general embodiments of the present invention overcomes the difficulties found in the prior art—including the unexpected step of requiring additional mixing of a new batch of material and the step of waiting for the material to reach a pasty polymerization stage. Many embodiments of this invention include methods that greatly decrease an operator's need to work in haste. Certain embodiments also minimize leakage of the material by providing steps in which a dam of material is first injected into the osseous structure in a controlled manner in order to prevent free flow of the material through openings or pores in the osseous structure. Typically, materials of varying viscosity, but including materials with higher viscosities than PMMA, are injected in a safe and technically proficient manner using the methods disclosed.

In accordance with some preferred forms of this invention such as the embodiment depicted in FIG. 1d, the dam 42 is allowed to cure and then a second aliquot of the restorative composition 40 is added to the dam 42, typically with a second catheter 41 after removal of the first catheter 31, as necessary. The dam 42 insures that all openings are closed with the composition 40 for leakage prevention. Typically, once the second aliquot of composition 40 has cured, additional aliquots of composition 40 are injected so that the space or opening is completely filled. It is appreciated that additional aliquots will not be necessary for all forms of this invention and that the number of aliquots may vary. Generally, the additional aliquots are added at pre-selected time intervals if the composition 40 is known to set within a certain time frame. More generally, the aliquots are added in a pre-selected amount.

In order to insure that the material is setting, not leaking and/or filling the desired space, it is within the scope of this invention that the location of the catheter 31 within the intraosseous space is monitored. When delivering a composition 40 into an intraosseous cavity such as a vertebra, the catheter's 31 placement is substantially close to, but not in contact with, the anterior wall. Some distance is necessary between the distal end of the catheter 31 and the wall so that the catheter 31 may deliver the compositions into the space. In those embodiments in which catheters are used with a side opening, the composition 40 can be radially dispersed into the space even if the distal end of the catheter is in contact with the anterior wall. During delivery of the composition 40, the catheter 31 may be slowly pulled back while the composition 40 fills the space. During a typical procedure, the catheter 31 can be monitored by a variety of means. More typically, if the catheter is comprised of metal, then it can be monitored by X-ray. The placement made by the catheter can also be monitored due to the radiopaque nature of a restorative composition. In other embodiments, the placement is monitored by fluoroscopy or endoscopy. Using these means, an operator reduces the chance that a composition will flow back in the needle or out of the intraosseous space. If a venous leak is detected, delivery is stopped.

It may be preferred in some embodiments to use catheters that have a front opening or side opening. The front opening allows direct injection of the material into the site. The side opening is useful for radial delivery of the composition within an osseous space and allows for 360° directional control of the material around the long axis of the catheter. To further aid in the delivery of the composition, the catheters are typically provided with markings or gradations along the shaft. Typically, these gradations aid in determining the depth of the catheter within the space. More typically, these markings are 1 cm apart. In other embodiments, the markings are placed at varying lengths suitable for each procedure.

Once the channel is created, the catheter 31 is filled with restorative material and inserted to the same depth created by the micro-reamer. The catheter 31 is easily visualized under fluoroscopy because of the radiopaque nature of restorative material. A small amount of the restorative material, less than 0.5 cc, is slowly injected under fluoroscopic control while checking for any venous leaks. Should a venous leak occur, the injection is immediately stopped, and the catheter 31 removed from the needle or cannula. In this way the access port to the vertebra remains open. After waiting an appropriate amount of time (between 2 to 4 minutes), a new catheter 41 is inserted and the injection resumed. Should another venous leak occur, the same procedure is repeated. Once there are no (more) venous leaks, the appropriate volume of material is injected. This technique is optimal for restorative materials with mix-on-demand characteristics. However, it can be used with any restorative material.

Figure 2B:
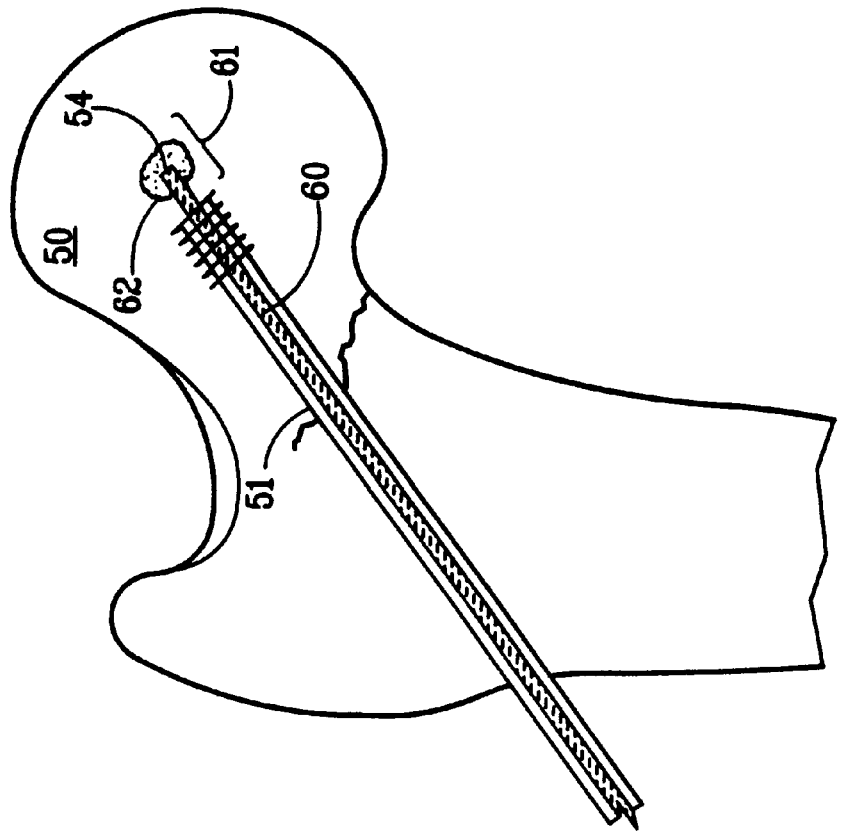
Figure 2A:
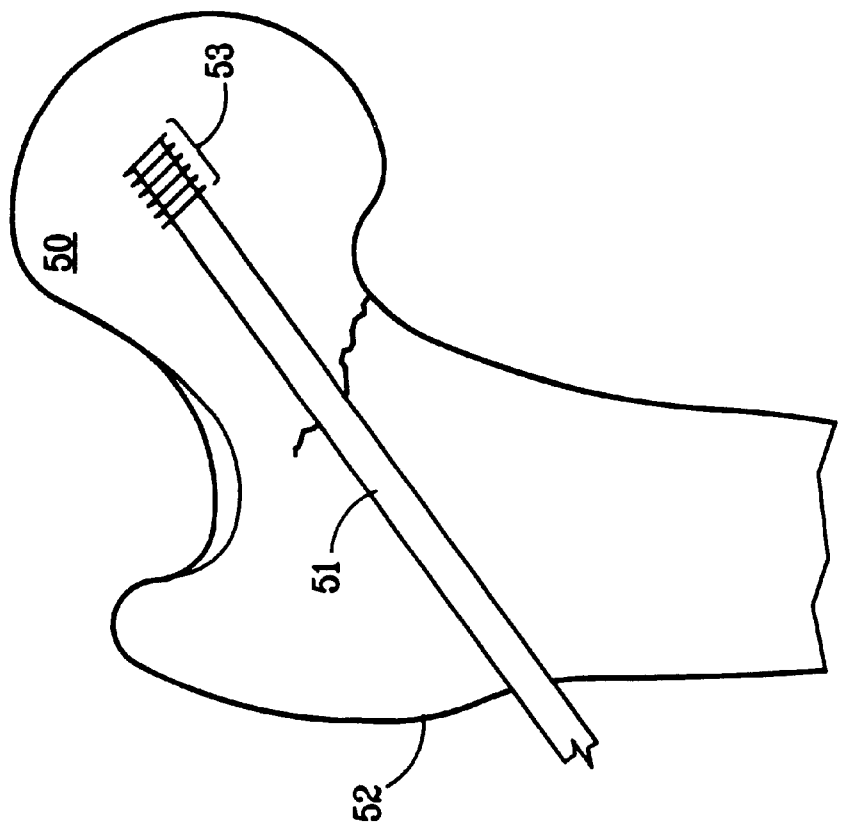

As described in accordance with FIGS. 2a–2d, one preferred embodiment of the present invention involves the percutaneous injection of restorative material into the femoral head 50 through a cannulated screw 51, which is inserted in a small opening along the lateral aspect of the neck of the femur 52 in the repair of compression hip fractures. The cannulated screw 51 is placed into a final position 53 (FIG. 2a) and then backed out from the final position (FIG. 2b) to allow room for the cement. A micro-delivery catheter 60 is then inserted through the cannulated screw 51 to allow for injection of the restorative material through the catheter 60 into an open void 61 in front of the screw 51. The tip 54 of the micro-delivery catheter 60 extends beyond the end of the screw 51 to allow for proper dispensing of material. A first aliquot of material 62 of approximately 1 cc is injected into the void 61 to serve as a dam for preventing leakage of the material through pores or openings in the bony structure. The micro-delivery catheter is removed, the first aliquot is allowed to set, and a second micro-delivery catheter 70 is inserted through the screw 51 to allow for injection of a second aliquot of material 71, which complements the first dose, in an amount sufficient to allow for screw purchase (approximately 1.5–3 cc) (FIG. 2c). Additional aliquots of material may be injected where necessary. Once the aliquots of material are delivered, the screw is advanced slowly into the un-polymerized restorative material the same number of turns minus one half turn used to back the screw out so as to insure that the screw is in its original position and also to insure that the threads of the screw do not displace the restorative material proximally. The restorative material is then allowed to set around the screw (FIG. 2d). The method of the present invention can also be employed with a cannulated screw in situations in which the guiding pin penetrates the cortex during repair and the hole needs to be sealed with a dam of material prior to the injection of additional material to repair the site.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for restoring an intraosseous space comprising:
 (a) accessing said space;
 (b) placing in said space a first aliquot of restorative composition; and
 (c) after a period of time sufficient for said first aliquot to set, placing in said space a second aliquot of restorative composition.

2. The method of claim 1 wherein the placement of said first aliquot is preselected so as to initiate restorative process.

3. The method of claim 1 wherein said pre-selection is of the location of said placement and said placement isolates said intraosseous space from surrounding tissue.

4. The method of claim 1 further comprising placing additional aliquots of restorative composition in said space.

5. The method of claim 1 wherein the further placements follow preselected time intervals.

6. The method of claim 1 wherein the further placements are of a preselected amount.

7. The method of claim 1 wherein said placement is via a syringe.

8. The method of claim 1 wherein said placement is via a catheter or cannula.

9. The method of claim 8 wherein the location of the catheter or cannula in the intraosseous space is monitored.

10. The method of claim 9 wherein the monitoring is via fluoroscopy.

11. The method of claim 9 wherein the monitoring is via endoscopy.

12. The method of claim 8 wherein the catheter has a distal end and at least one placement orifice disposed proximate to said distal end, said placement orifice being adapted for dispensing the restorative composition radially from the catheter.

13. The method of claim 1 wherein said space is accessed via a drill or micro-reamer.

14. The method of claim 1 wherein said space is accessed via a knife or sharp instrument.

15. The method of claim 1 wherein said space is accessed via a needle or cannula.

* * * * *

UNITED STATES PATENT AND TRADEMARK OFFICE
CERTIFICATE OF CORRECTION

PATENT NO.    : 6,375,659 B1
DATED         : April 23, 2002
INVENTOR(S)   : Erbe et al.

It is certified that error appears in the above-identified patent and that said Letters Patent is hereby corrected as shown below:

Column 3,
Line 24, please delete "FIGS. 2*a*-2*f*" and insert therefor -- FIGS. 2*a*-2*d* --;
Lines 44 and 45, please delete "(see FIGS. 2*a* through 2*f*)." and insert therefor -- (see FIGS. 2*a* through 2*d*). --.

Signed and Sealed this

Fifteenth Day of October, 2002

*Attest:*

JAMES E. ROGAN
*Attesting Officer*  *Director of the United States Patent and Trademark Office*

UNITED STATES PATENT AND TRADEMARK OFFICE
CERTIFICATE OF CORRECTION

PATENT NO. : 6,375,659 B1 Page 1 of 1
APPLICATION NO. : 09/788930
DATED : April 23, 2002
INVENTOR(S) : Erbe et al.

It is certified that error appears in the above-identified patent and that said Letters Patent is hereby corrected as shown below:

column 6
line 34: delete "1" and insert --2--
line 39: delete "1" and insert --4--
line 41: delete "1" and insert --4--

Signed and Sealed this

Twenty-fifth Day of December, 2007

JON W. DUDAS
*Director of the United States Patent and Trademark Office*

(12) EX PARTE REEXAMINATION CERTIFICATE (8898th)
United States Patent
Erbe et al.

(10) Number: US 6,375,659 C1
(45) Certificate Issued: Mar. 13, 2012

(54) METHOD FOR DELIVERY OF BIOCOMPATIBLE MATERIAL

(75) Inventors: Erik M. Erbe, Berwyn, PA (US); Antony Kobilish, Malvern, PA (US); Maarten Persenaire, Phoenixville, PA (US)

(73) Assignee: Orthovita, Inc., Malvern, PA (US)

Reexamination Request:
No. 90/010,652, Oct. 16, 2009

Reexamination Certificate for:
Patent No.: 6,375,659
Issued: Apr. 23, 2002
Appl. No.: 09/788,930
Filed: Feb. 20, 2001

Certificate of Correction issued Oct. 15, 2002.

Certificate of Correction issued Dec. 25, 2007.

(51) Int. Cl.
*A61F 5/04* (2006.01)
*A61B 17/88* (2006.01)

(52) U.S. Cl. .............. 606/94; 606/93; 623/23.62; 623/23.73

(58) Field of Classification Search .................. None
See application file for complete search history.

(56) References Cited

To view the complete listing of prior art documents cited during the proceeding for Reexamination Control Number 90/010,652, please refer to the USPTO's public Patent Application Information Retrieval (PAIR) system under the Display References tab.

*Primary Examiner* — Jeanne M Clark

(57) ABSTRACT

Novel methods for the delivery of biocompatible material to intraosseous spaces are provided comprising accessing a space, placing a first aliquot of restorative material into the space, and after a period of time sufficient for first aliquot to set, placing a second aliquot into the space.

At the time of issuance and publication of this certificate, the patent remains subject to pending reissue application number 12/967,537 filed Dec. 14, 2010. The claim content of the patent may be subsequently revised if a reissue patent is issued from the reissue application.

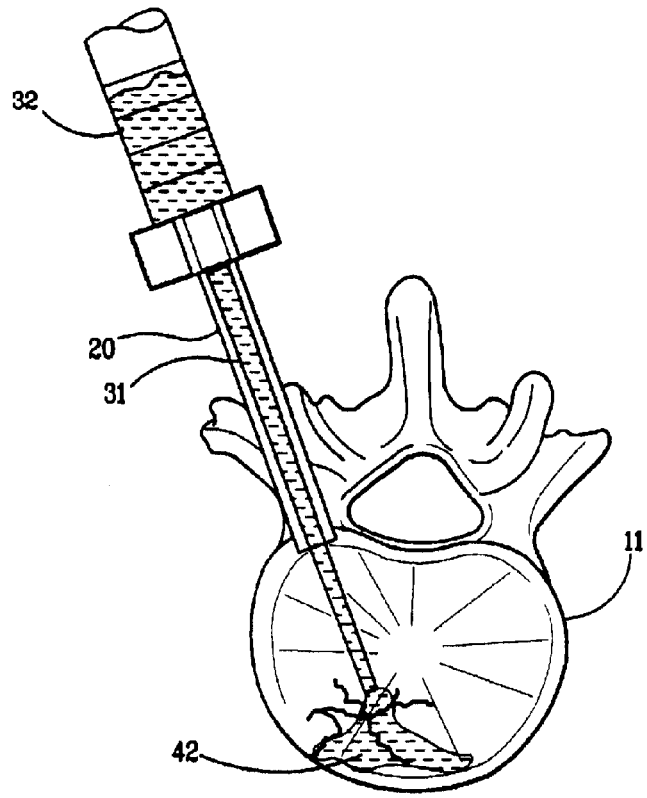

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claim 1 is cancelled.

Claims 2-15 were not reexamined.

* * * * *